United States Patent [19]

Schwaiger et al.

[11] Patent Number: 4,851,542
[45] Date of Patent: Jul. 25, 1989

[54] N₁-SUBSTITUTED 1H-BENZYTRIAZOLE HYDROXYETHYL SULFONE COMPOUNDS, A PROCESS FOR THEIR PREPARATION AND THEIR USE FOR THE PREPARATION OF DYESTUFFS

[75] Inventors: Günther Schwaiger, Frankfurt am Main; Hartmut Springer, Königstein, both of Fed. Rep. of Germany

[73] Assignee: Hoechst Aktiengesellschaft, Frankfurt am Main, Fed. Rep. of Germany

[21] Appl. No.: 76,749

[22] Filed: Jul. 23, 1987

[30] Foreign Application Priority Data

Jul. 26, 1986 [DE] Fed. Rep. of Germany ....... 3625386

[51] Int. Cl.⁴ .............................................. A61K 31/41
[52] U.S. Cl. ..................................... 548/259; 544/76; 548/260; 548/261
[58] Field of Search ................. 548/257, 259, 260, 261

[56] References Cited

U.S. PATENT DOCUMENTS

| 3,267,113 | 8/1966 | Carboni | 548/257 |
| 4,182,713 | 1/1980 | Goebel | 548/259 |
| 4,629,788 | 12/1986 | Jaeger et al. | 544/76 |

FOREIGN PATENT DOCUMENTS

| 0141996 | 5/1985 | European Pat. Off. . | |
| 0222098 | 5/1987 | European Pat. Off. . | |
| 3625347 | 3/1987 | Fed. Rep. of Germany | 548/259 |
| 2487994 | 2/1982 | France | 548/260 |

*Primary Examiner*—Donald G. Daus
*Assistant Examiner*—Mark W. Noel

[57] ABSTRACT

N₁-substituted 1H-benzotriazole hydroxyethyl sulfone compounds, a process for their preparation and their use for the preparation of dyestuffs. Compounds of the general formula

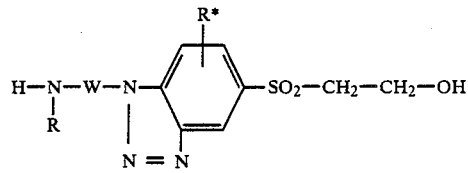

in which R is hydrogen or alkyl which has 1 to 6 carbon atoms and can be substituted by hydroxy, sulfo, carboxy, phosphono and/or cyano, W denotes a divalent, optionally substituted aliphatic radical, ($C_5$–$C_{10}$)-cycloaliphatic radical which is optionally substituted by alkyl, aliphatic-($C_5$–$C_8$)-cycloaliphatic radical which is optionally substituted by alkyl, optionally substituted araliphatic radical or optionally substituted aromatic carbocyclic radical, it being possible for the aliphatic radicals in W to be interrupted by hetero groups of the formulae —O—, —S—, —SO₂—, —CO—, 1,4-piperidino, —NH— and —N(R')— in which R' is an alkyl group which has 1 to 6 carbon atoms and can be substituted, or is an alkanoyl group having 2 to 5 C atoms, and/or for the aliphatic radicals and aryl radicals to be attached to one another through such a hetero group, and R* denotes hydrogen, alkyl having 1 to 6 carbon atoms, alkoxy having 1 to 5 carbon atoms, halogen, carboxy or sulfo.

They are used as intermediates for the preparation of dyestuffs, such as fiber-reactive triphendioxazine dyestuffs, and can be prepared by reducing the nitro group in a compound of the general formula

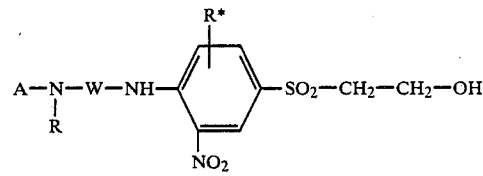

in which R, R* and W have the abovementioned meaning and A is a hydrogen atom or an acyl radical, to the amino group and diazotizing this amino group, whereupon cyclization takes place to give the benzotriazole, and, if necessary, subsequently eliminating the acyl radical by hydrolysis.

10 Claims, No Drawings

N₁-SUBSTITUTED 1H-BENZYTRIAZOLE HYDROXYETHYL SULFONE COMPOUNDS, A PROCESS FOR THEIR PREPARATION AND THEIR USE FOR THE PREPARATION OF DYESTUFFS

The invention falls within the technical field of intermediates.

The present invention relates to compounds of the general formula (1)

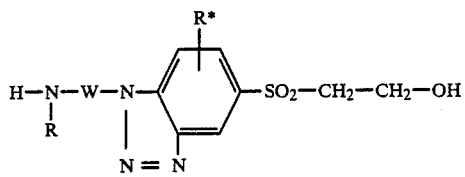

in which

R is a hydrogen atom or an alkyl group which has 1 to 6 carbon atoms and can be substituted by one or two substituents, preferably one substituent, belonging to the group comprising hydroxy, sulfo, carboxy, phosphono and cyano, W denotes a divalent, optionally substituted aliphatic radical, ($C_5$-$C_{10}$)-cycloaliphatic radical which is optionally substituted by alkyl, aliphatic-($C_5$-$C_8$)-cycloaliphatic radical which is optionally substituted by alkyl, optionally substituted araliphatic radical or optionally substituted aromatic-carbocyclic radical, it being possible for the aliphatic radicals in W to be interrupted by hetero groups, preferably one or two hetero groups, selected from the groups of the formulae —O—, —S—, —SO₂—, —CO—, 1,4-piperidino, —NH— and —N(R'—) in which R' is an alkyl group which has 1 to 6 carbon atoms, preferably 1 to 4 carbon atoms, such as, in particular, the methyl or ethyl group, and which can be substituted, or is an alkanoyl group having 2 to 5 carbon atoms, such as the acetyl group, and/or it being possible for the aliphatic radicals and aryl radicals to be attached to one another through such a hetero group, and R* denotes a hydrogen atom or an alkyl group having 1 to 6 carbon atoms, preferably 1 to 4 carbon atoms, such as, in particular, methyl and ethyl, an alkoxy group having 1 to 5 carbon atoms, preferably 1 to 4 carbon atoms, such as, in particular, methoxy or ethoxy, a halogen atom, such as fluorine and bromine and, in particular, chlorine, or a carboxy or sulfo group, and to the use thereof for the preparation of fiber-reactive dyestuffs.

In the preceding and following text, a carboxy group denotes a group of the general formula —COOM, a sulfo group denotes a group of the general formula —SO₃M and a phosphono group denotes a group of the general formula —PO₃M₂ in which M denotes a hydrogen atom or an alkali metal, such as sodium, potassium or lithium.

The present invention also relates to a process for the preparation of the compounds of the general formula (1), which comprises reducing the nitro group in a compound of the general formula (2)

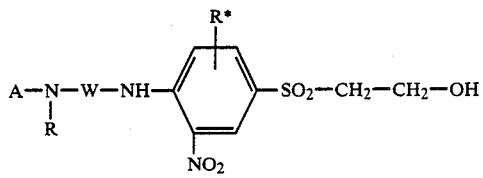

in which R, R* and W have the abovementioned meanings and A is a hydrogen atom or an acyl radical, such as an alkanoyl radical having 2 to 5 carbon atoms, such as the acetyl radical, or is a benzoyl radical, it being necessary for A to represent an acyl radical in the event that W denotes an aromatic-carbocyclic radical, in a manner which is customary per se and analogous to known processes, to give the amino group, and diazotizing the compound obtained therefrom of the general formula (3)

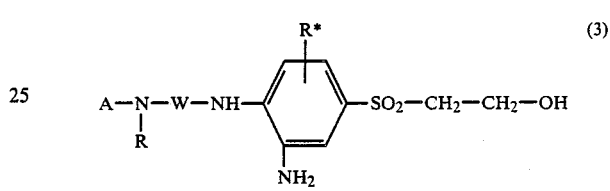

in which A, R, R* and W have the abovementioned meanings, by a procedure of diazotization which is customary per se, for example by means of sodium nitrite in an aqueous acid, preferably hydrochloric acid, medium at a temperature between −10° C. and +20° C., and, if appropriate, in the event that the group A in formula (3) should denote an acyl radical, subsequently deacylating the benzotriazole compound of the general formula (1) which has been obtained as an acyl derivative to give the benzotriazole compound of the general formula (1) analogously to known methods, for example in an aqueous medium at a temperature between about 90° and 100° C. and at a pH higher than 12, such as by means of a sodium hydroxide solution containing a three-fold to six-fold amount of NaOH, but preferably in an acid, for example hydrochloric acid, aqueous medium at a pH value below 2. When the compounds of the formula (3) are diazotized, cyclization of the diazonium group formed with the amino group in the ortho-position takes place.

The compounds of the general formula (2) can also be prepared in a manner according to the invention by reacting a compound of the general formula (4)

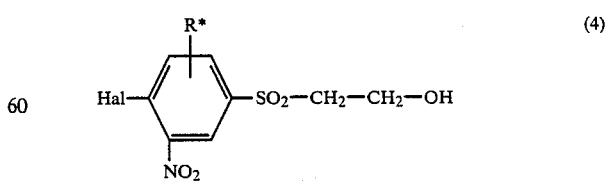

in which R* has the abovementioned meaning and Hal denotes a fluorine or bromine atom or, preferably, a chlorine atom, with a compound of the general formula (5)

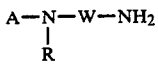

in which A, R and W have the abovementioned meanings, in a solvent suitable for these reactants, in the presence of an acid-binding agent and at a temperature between 30° and 120° C., preferably between 70° and 90° C.

The starting compounds of the general formula (4) are known per se (see, for example, German Pat. No. 859,462, Example 5); compounds corresponding to the general formula (4) which have not yet been described per se can be prepared analogously to the known compounds in the manner familiar to those skilled in the art, for example synthesized by nitrating a corresponding (β-hydroxyethylsulfonyl)-chlorobenzene compound or by reducing a corresponding 4-chloro-3-nitrobenzenesulfochloride compound by means of sodium sulfite to give the corresponding sulfinic acid and subsequently oxethylating the sulfinic acid to give the β-hydroxyethylsulfonyl compound.

Examples of starting compounds corresponding to the general formula (5) are 1,2-diaminoethane, 1,3-diaminopropane, 1,4-diaminobutane, 1,5-diaminopentane, 1,6-diaminohexane, 1,2-diaminopropane, 1,2-diaminobutane, 1,3-diaminobutane, the N-acyl compounds, such as the N-acetyl and N-benzoyl compounds, of 1-amino-3-methylaminopropane, 1,3-diamino-2-methylpropane, 1,3-diamino-2-hydroxypropane, 1,5-diamino-2-carboxypentane, 1,3-diamino-2-phenylpropane or its derivative which is sulfo-substituted in the benzene radical, and also compounds corresponding to a general formula (a), (b), (c) and (d)

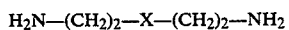  (a)

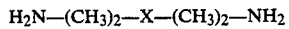  (b)

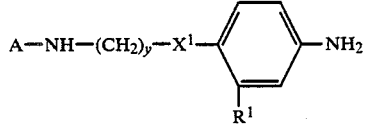  (c)

  (d)

in which

X denotes an oxygen atom, a sulfur atom, a sulfonyl group or a group of the formula —NH—, —N(CH$_3$)— or —N(COCH$_3$)—, R$^1$ represents a hydrogen atom or a sulfo group, A has the abovementioned meaning, n is the number 2, 3 or 4, X$^1$ represents the group —NH— or an oxygen atom and y denotes the number 2 or 3, and also 1,3-cyclohexylenediamine, 1,4-cyclohexylenediamine, bis-(4-aminocyclohex-1-yl)-methane, 1,8-di-(aminomethyl)-naphthalene, 1,4-di-(aminomethyl)-benzene, 1,3-di-(aminomethyl)-benzene, N,N'-bis-(β-aminoethyl)-1,4-piperidine, 1,4-phenylenediamine, 1,3-phenylenediamine, 4-aminobenzylamine, 4-aminophenethylamine and the corresponding N-monoacyl derivatives of such compounds. Of these, 1,2-diaminoethane, 1,3-diaminopropane, 1,4-diaminobutane and 1,2-diaminopropane are preferred.

Since hydrogen chloride is eliminated in the reaction of the compounds (4) with the compounds (5), it is necessary to carry out the reaction in the presence of an acid-binding agent. Agents suitable for this purpose are either inorganic compounds, such as, for example, sodium hydroxide, potassium hydroxide, sodium carbonate, calcium carbonate, magnesium oxide, sodium acetate or potassium acetate, or organic basic compounds, such as, for example, trialkylamines containing alkyl radicals having 1 to 4 carbon atoms, such as, for example, trimethylamine and triethylamine, or pyridine, quinoline, the picolines and morpholine. The acid-binding agent must be present in each case in at least an amount equivalent to the monohalogen compound (4). If the amino compound (5) is a compound having an adequately basic reaction, such as, for example, ethylenediamine, and if this compound is employed in an adequate excess, this compound then acts as an acid acceptor, as a result of which the addition of a separate inorganic or organic acid-binding agent is unnecessary.

Examples of suitable solvents which can be used as the reaction medium in the reaction of (4) with (5) are water, alkanols having 1 to 4 carbon atoms, such as methanol, ethanol, propanol and isopropanol, dioxane, toluene, the xylenes, chlorobenzene, o-dichlorobenzene, m-dichlorobenzene, dimethylformamide or N-methylpyrrolidone. If one of the two reactants (4) or (5) or both of them are not completely soluble in the solvent used, the reaction takes place partly in suspension, which does not affect it adversely. It is also possible, however, to employ the compound (5) as the solvent by using it in a sufficient excess.

If a solvent is used in which the two reactants (4) and (5) are each completely soluble, it is suitable to react the compounds (4) and (5) in a molar ratio of 1:(1–2.5). Although the use of a larger excess of the compound (5) is possible, it affords no further advantage and is therefore not advisable.

If a solvent is used in which one or both of the reactants (4) and (5) are not completely soluble, or if excess (5) is used as the solvent, it is suitable to react the compound (5) with the compound (4) in an amount by weight of 1 to 4 times, relative to the compound (4). Here too, the use of a larger excess of (5) is possible but not advisable.

After being synthesized, the nitro compound of the general formula (2) can be isolated in a simple manner by crystallization from this reaction mixture and subsequent filtration, optionally after distilling partially or completely the solvent or the excess reagent (5), which can advantageously be recovered for further reactions, and then mixing the eventually concentrated reaction mixture with cold water which, if appropriate, contains an electrolyte salt, such as sodium chloride, potassium chloride or sodium sulfate. The product which crystallizes out in this way can be isolated by filtration, if appropriate after acidification with mineral acid. The subsequent reduction of the nitro compound (2) to the corresponding amino compound (3) can be carried out in a manner known per se by catalytic hydrogenation with hydrogen over known catalysts, such as palladium, platinum or Raney nickel, at a temperature between 20° and 150° C., preferably between 50° and 110° C., and under an elevated pressure, for example between 30 and 100 bar, preferably between 40 and 55 bar, or by reduction by the Béchamp method using iron in an acid or alkaline medium, preferably an acid medium, for example using iron in ethanol/glacial acetic acid. It is particularly advantageous to subject the nitro compound (2) which can be obtained from the reaction of the compounds (4) and (5) to catalytic hydrogenation directly, without intermediate isolation thereof. This makes it possible to reduce energy and effluent costs. The reduction of (2) to (3), whether carried out catalytically or by the Béchamp method, is appropriately carried out in a suitable solvent, such as water, methanol or ethanol, or in a mixture of water and methanol or water and ethanol, since this makes it possible to induce the amino compounds (3) to crystallize in a simple manner by cooling, if appropriate after acidification with mineral acid, in the form of the free amino compounds or in the form of salts thereof with mineral acids; if appropriate, they can also be salted out with sodium chloride. The subsequent separation is then carried out by filtration, and the mother liquors can be re-used for subsequent hydrogenation batches and, if appropriate, recycled for this purpose. It is also possible to recover the organic solvent from the mother liquors by simple distillation under normal pressure.

The procedures according to the invention make it possible to obtain the new compounds of the general formula (1) in good to very good yields. They constitute new, valuable intermediates for the preparation of fiber-reactive dyestuffs, in particular fiber-reactive triphendioxazine dyestuffs, such as, for example, the preparation of dyestuffs of the general formula (A)

stuffs afford dyeings in clear blue and fast shades on cotton by the dyeing procedures customary in the art for fiber-reactive dyestuffs.

The use, according to the invention, of the compounds (1) as intermediates for the synthesis of fiber-reactive dyestuffs is carried out, for example, by first reacting the compound (1) with a chloronitro compound, for example with 2-sulfo-4-nitrochlorobenzene, 2-(β-sulfoethylsulfonyl)-4-nitrochlorobenzene or 2-(β-hydroxyethylsulfonyl)-4-nitrochlorobenzene, to give a compound of the general formula (6)

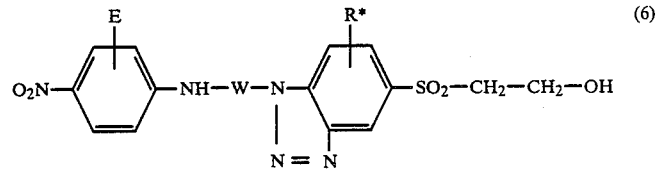

in which W, R* and E have the abovementioned meanings or E is also a β-hydroxyethylsulfonyl group (it being possible to carry out the reaction of the amino compound with the chlorobenzene compound analogously to the instructions above by a procedure which is known per se), and to reduce the nitro group in this compound (6) by a procedure which is known per se, such as that described above, for example, to give the amino group in the compounds of the general formula (7)

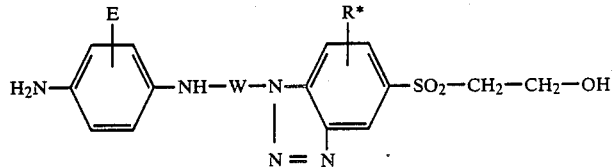

in which W, R* and E have the abovementioned meanings. The amino compound of the general formula (7) can then be reacted with 2,3,5,6-tetrachloro-1,4-benzoquinone by a procedure, known per se, of the preparation of fiber-reactive triphendioxazine compounds (see, for example, European Patent Application Publication No. 0,168,751 A1) with oxidative cyclization and simultaneous or subsequent sulfation in sulfuric acid containing sulfur trioxide to give the dyestuffs of the formula (A).

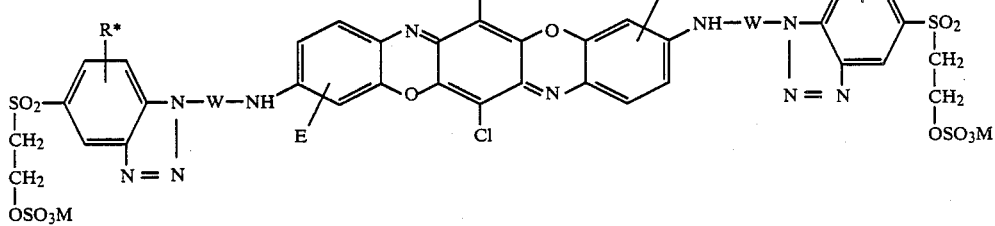

in which W and R* have the abovementioned meanings, M denotes an alkali metal and E denotes a hydrogen atom or a sulfo, carboxy, $C_1$-$C_4$-alkylsulfonyl or sulfo-$C_1$-$C_4$-alkylsulfonyl group or a β-sulfatoethylsulfonyl group. An example of particularly advantageous triphendioxazine dyestuffs corresponding to the general formula (A) are dyestuffs in which E is a sulfo group and W is an ethylene or n-propylene group; these dye-

EXAMPLE 1

(a) 530 parts of 2-nitro-4-(β-hydroxyethylsulfonyl)-chlorobenzene are introduced slowly, at a temperature between 70° and 80° C., into 620 parts of ethylenediamine; the mixture is kept at this temperature for some time and is then, after quantitative reaction has been reached, stirred into water. The compound of the formula

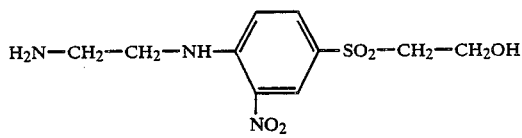

which has been precipitated, is isolated by filtration and dried. It is obtained in a good yield and high purity (melting point 146°/147° C.) and gives the following data in $^1$H-NMR analysis (in d$_6$-DMSO using TMS as internal standard):

δ=2.83 ppm (t,2H); 3.44 ppm (m,2H); 3.7 ppm (m,2H); 7.27 ppm (d,1H); 7.9 ppm (dd,1H); 8.49 ppm (d,1H); mobile protons at 1.7 ppm (NH$_2$), 4.8 ppm (OH) and 8.8 ppm (NH).

(b) The nitro compound obtained under (a) is reduced to the aniline compound by hydrogenating 290 parts of the nitro compound in 1200 parts of water in the presence of a Pd-on-charcoal catalyst in an autoclave at a temperature of up to 100° C. and under a hydrogen pressure of 50 bar. The catalyst is then filtered off; the amino compound obtained can be processed further in the filtrate without further treatment.

A sample of the aniline compound obtained of the formula

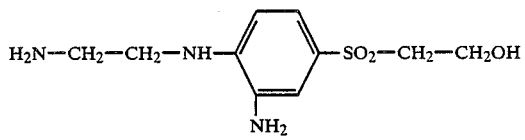

is isolated and has a melting point of 169°–172° C. and gives the following data in $^1$H-NMR analysis (in d$_6$-DMSO using TMS as internal standard):

δ=2.84 ppm (t,2H); 3.2 ppm (m,4H); 3.6 ppm (m,2H); 6.53 ppm (dd,1H); 6.96 ppm (d,1h); 7.0 ppm (dd,1H); mobile protons at 4–5 ppm (NH$_2$,OH) and 5.45 ppm (NH).

(c) 260 parts of β-[4-(β-hydroxyethylsulfonyl)-2-aminophenylamino]-ethylamine in about 1800 parts of an aqueous solution of hydrochloric acid are diazotized in a customary manner at 0° to 5° C. by means of an aqueous solution of sodium nitrite. Cyclization takes place immediately and quantitatively. A sample of the compound of the formula

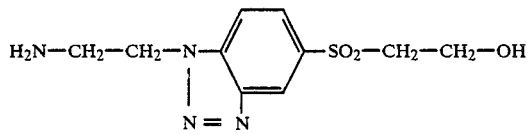

is isolated and gives the following data in $^1$H-NMR analysis (in d$_6$-DMSO using TMS as internal standard):

δ=3.06 ppm (t,2H); 3.54 ppm (m,2H); 3.7 ppm (m,2H); 4.72 ppm (t,2H); 8.0 ppm (dd,1H); 8.16 ppm (dd,1H); 8.6 ppm (m,1H); mobile protons (OH, NH$_2$).

EXAMPLE 2

(a) 530 parts of 2-nitro-4-(β-hydroxyethylsulfonyl)-chlorobenzene are introduced slowly into 750 parts of 1,3-propylenediamine at a temperature between 70° and 80° C.; the mixture is kept at this temperature for some time and, when quantitative reaction has been reached, is then stirred into water. The compound of the formula

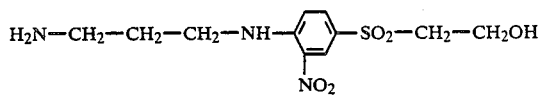

which is precipitated, is isolated by filtration and dried. It is obtained in good yield and high purity, melting point 110°/112° C., and gives the following data in $^1$H-NMR analysis (in d$_6$-DMSO using TMS as internal standard):

δ=1.7 ppm (m,2H); 2.66 ppm (t,2H); 3.5 ppm (m,4H); 3.68 ppm (m,2H); 7.25 ppm (d,1H); 7.9 ppm (dd,1H); 8.5 ppm (d,1H); mobile protons (NH$_2$, OH, NH) at approx. 5 ppm.

(b) The nitro compound obtained under (a) is reduced to the aniline compound by hydrogenating 303 parts of the nitro compound in 1200 parts of water in the presence of a Pd-on-charcoal catalyst in an autoclave at a temperature of up to 100° C. and under a hydrogen pressure of 50 bar. The catalyst is then filtered off; the resulting amino compound can be processed further in the filtrate without further treatment.

A sample of the aniline compound obtained of the formula

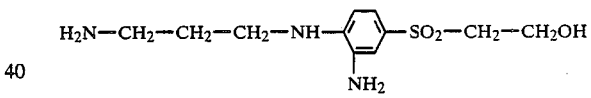

is isolated and gives the following data in $^1$H-NMR analysis (in d$_6$-DMSO using TMS as internal standard):

δ=1.9 ppm (m,2H); 2.88 ppm (t,2H); 3.2 ppm (m,4H); 3.58 ppm (m,2H); 6.51 ppm (dd,1H); 6.92 ppm (d,1H); 6.96 ppm (dd,1H); mobile protons at 4.9 ppm (OH), 5.2 ppm (NH$_2$), 5.74 ppm (NH) and 8.2 ppm (NH$_2$).

(c) 260 parts of γ-[4-(β-hydroxyethylsulfonyl)-2-aminophenylamino]-n-propylamine in about 1800 parts of an aqueous solution of hydrochloric acid are diazotized in a customary manner at 0° to 5° C. by means of an aqueous solution of sodium nitrite. Cyclizatioin takes place immediately and quantitatively. A sample of the compound of the formula

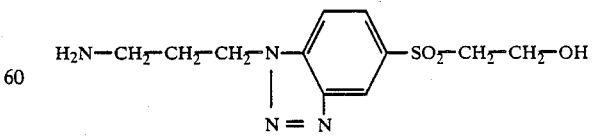

is isolated and gives the following data in $^1$H-NMR analysis (in d$_6$-DMSO using TMS as internal standard):

δ=2.24 ppm (m,2H); 2.85 ppm (m,2H); 3.6 ppm (m,4H); 4.92 ppm (t,2H); 8.04 ppm (dd,1H); 8.27 ppm (d,1H); 8.6 ppm (s,1H); mobile protons (OH,NH$_2$).

EXAMPLE 3

132.8 parts of 4-(β-hydroxyethylsulfonyl)-2-nitrochlorobenzene are introduced, in the course of 30 minutes, into a solution of 118.8 parts of 1,4-phenylenediamine in 500 parts by volume of methanol at 65° C. and under an atmosphere of nitrogen. Stirring is continued for a further 4 hours at this temperature, the mixture is allowed to cool to room temperature and the reaction product is crystallized out by adding 1000 parts by volume of ice water 4-(β-hydroxyethylsulfonyl)-2-nitro-4'-amino-diphenylamine is obtained in high yield by filtration with suction and drying. It is N-acylated at 50° C. with the equimolar amount of acetic anhydride, for ex. in glacial acetic acid; this acetamino compound, which has a melting point of 193°/194° C., is then reduced to the anilino compound of the formula

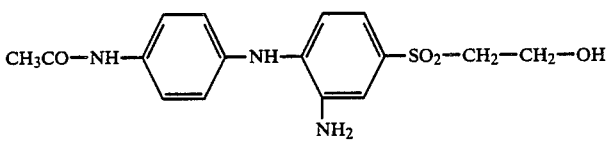

(m.p.: 183°/184° C.) which is converted, by diazotization and subsequent acid deacylation in accordance with customary procedures, into the compound, according to the invention, of the formula

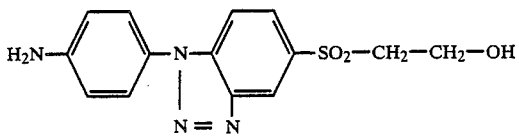

The compound according to the invention has a melting point of 177° C. It gives the following data in $^1$H-NMR analysis (in $d_6$-DMSO with TMS as internal standard):

$\delta$=3.6 ppm (t,2H); 3.8 ppm (m,2H); 4.9 ppm (t,OH); 5.7 ppm (s,NH$_2$); 6.8 ppm (d,2H); 7.5 ppm (d,2H); 8.0 ppm (d,1H); 8.1 ppm (d,1H); 8.7 ppm (s,1H).

It is also preferable to use 4-aminoacetanilide as the starting compound instead of 1,4-phenylenediamine. In this case, the acid-binding agent used is, for example, sodium acetate, triethylamine or triethanolamine; the subsequent N-acetylation is consequently unnecessary.

EXAMPLE 4

The procedure of Example 3 is used to prepare a compound according to the invention, but an equal amount of 1,3-phenylenediamine or, preferably, 3-aminoacetanilide is employed instead of 1,4-phenylenediamine. The compound, according to the invention, of the formula

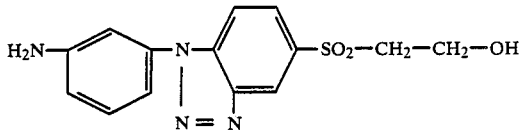

is obtained in this manner.

USE EXAMPLE 1

The compound, according to the invention, described in Example (1c) can be processed further as follows to give a dyestuff:

(a) 259 parts of the sodium salt of 5-nitro-2-chlorobenzenesulfonic acid are first added, at a temperature of 40° C., to a mixture of 270 parts of 5-(β-hydroxyethylsulfonyl)-1-(β-aminoethyl)-benzotriazole in 1000 parts of water and 500 parts of triethanolamine (the benzotriazole compound can also be employed, without further treatment, in the form of the solution obtained in accordance with Example 1c)). The mixture is heated to 100° to 110° C. in the course of two hours, during which part of the water distils off. The mixture is stirred for a further 10 hours at 115° to 120° C. to achieve quantitative reaction, and 3000 parts of water are then added at 100° C., and the solution is clarified at 80° to 90° C. On cooling, the sodium salt of 4-[β-(5'-β'-hydroxyethylsulfonylbenzotriazol-1'-yl)-ethylamino]-3-sulfonitrobenzene crystallizes out from the aqueous medium in a high yield and purity. The nitro compound gives the following data in $^1$H-NMR analysis (in $d_6$-DMSO with TMS as internal standard):

$\delta$=3.5 ppm (m,2H); 3.64 ppm (t,2H); 3.95 ppm (m,2H); 4.82 ppm (t,OH); 5.0 ppm (t,2H); 6.69 ppm (d,1H); 7.57 ppm (t,NH); 7.95 ppm (m,2H); 8.16 ppm (m,1H); 8.3 ppm (d,1H); 8.57 ppm (d,1H).

The nitro compound is then reduced to the aniline compound by catalytic hydrogenation by dissolving 236 parts of the nitro compound in 1000 parts of water and hydrogenating it in the presence of a Pd-on-charcoal catalyst in an autoclave at a temperature of up to 100° C. and under a hydrogen pressure of 50 bar. The catalyst is then filtered off and the filtrate is cooled and acidified. The aniline compound of the formula

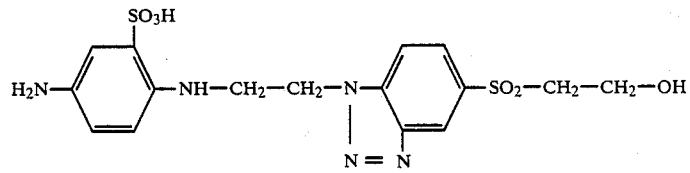

crystallizes out therefrom in a good yield and high purity.

(b) 441 parts of the aniline compound obtained under (a) are dissolved in 2000 parts of water at pH 6° and 60° C. 124 parts of chloranil are introduced, the pH being kept at a value of 6.5 by means of about 90 parts of sodium bicarbonate and the reaction temperature being kept at about 65° C. The mixture is stirred for a further 6 hours and the reaction product is then clarified at about 65° C., precipitated by means of a little sodium chloride, filtered off with suction, washed with 1000 parts of 10% strength aqueous sodium chloride solution and dried at 70° C. under reduced pressure.

(c) 105 parts of the product obtained under (b) are introduced at a temperature between 20° and 25° C. into 750 parts of 13% strength oleum. The reaction mixture is then stirred for about a further 3 hours at this temperature; 48 parts of sodium peroxodisulfate are then introduced at such a rate that the reaction temperature can be kept at 20° to 25° C. The mixture is stirred for a further 10 hours at this temperature and is then run onto ice, and the compound, according to the invention, which has been precipitated is filtered off and redissolved in about 1000 parts of water, the pH of which is adjusted to a value of 5 with sodium carbonate, and the compound is salted out by means of sodium chloride, if necessary after clarifying the solution beforehand in a customary manner.

The triphendioxazine compound according to the invention can also be obtained in the form of its sodium salt by evaporating or spray-drying the clarified synthesis solution. Expressed in the form of the free acid, it has the probable formula

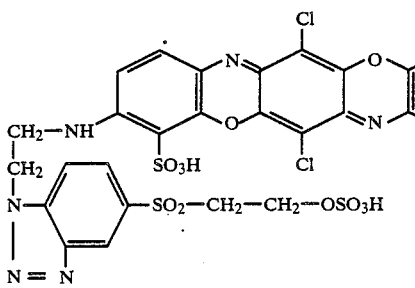
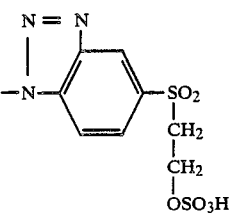

(each of the sulfo groups can also be attached in the other ortho-position relative to the benzotriazolylethylamino group, but is more probably located in the position indicated in the above formula). This compound according to the invention possesses good fiber-reactive properties as a dyestuff. It dyes the materials mentioned in the description, in particular cellulose fiber materials, such as cotton, by the procedures which are customary and known in the art for the application and fixation of fiber-reactive dyestuffs, in deep, clear, reddish-tinged blue shades (corresponding to the color coordinate 13 of the Color Index Hue Indication Chart) having good fastness properties such as, in particular, good fastness to light of the dry or moist, moistened with drinking water, dyeing, good fastness to light in alkaline perspiration, fastness to chlorinated water, fastness to hypochlorite, fastness to alkaline perspiration, fastness to washing, even in the presence of perborates, fastness to wet storage and resistance to acid fading. In aqueous solution, it displays an absorption maximum in the visible range at 612 nm.

USE EXAMPLE 2

The compound, according to the invention, described in Example (2c) can be processed further as follows to give a triphendioxazine dyestuff:

An aqueous acid solution, obtained as in Example (2c), of 285 parts of 5-(β-hydroxyethylsulfonyl)-1-(γ-aminopropyl)-benzotriazole and 500 parts of triethanolamine is warmed to 40° C. and 259 parts of the sodium salt of 5-nitro-2-chlorobenzenesulfonic acid are added. The mixture is heated to 100° to 110° C. in the course of two hours, during which time part of the water distils off. The mixture is stirred at 115° to 120° C. for a further 10 hours in order to achieve quantitative reaction, and 3000 parts of water are then added at 100° C. and the solution is clarified at 80° to 90° C. On cooling, the sodium salt of 4-[γ-(5'-β'-hydroxyethylsulfonylbenzotriazol-1'-yl)-propylamino]-3-sulfonitrobenzene crystallizes out from the aqueous medium in a high yield and purity. The nitro compound gives the following data in $^1$H-NMR analysis (in d$_6$-DMSO with TMS as internal standard):

δ=2.25 ppm (m,2H); 3.32 ppm (m,2H); 3.54 ppm (m,2H); 3.66 ppm (m,2H); 4.9 ppm (m,OH,2H); 6.9 ppm (d,1H); 7.47 ppm (t,NH); 8.0 ppm (m,2H); 8.20 ppm (m,1H); 8.37 ppm (d,1H); 8.62 ppm (d,1H).

The nitro compound obtained in this way can then be reduced to the aniline compound of the formula

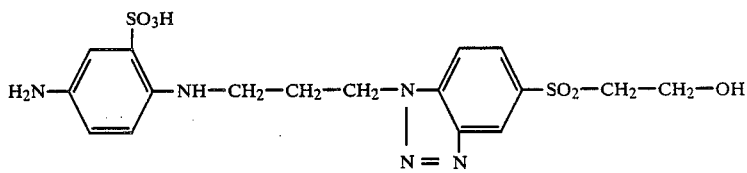

in accordance with the instructions of Example (1a), and the product can then be converted in accordance with the instructions of Use Example (1b) and (1c) into a valuable blue triphendioxazine dyestuff.

We claim:
1. A compound corresponding to the formula

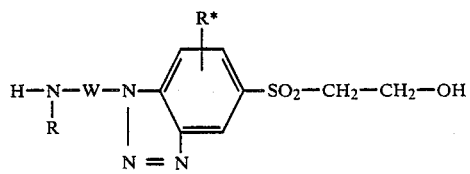

in which

R is hydrogen or is alkyl of 1 to 6 carbon atoms unsubstituted or substituted by one or two substituents belonging to the group comprising hydroxy, sulfo, carboxy, phosphono and cyano, W is 1,2-ethylene, 1,3-propylene, 1,4-butylene, 1,5-pentylene, 1,6-hexylene, 1,2-propylene, 1,2-butylene, 1,3-butylene, 2-methyl-1,3-propylene, 2-hydroxy-1,3-propylene, 2-carboxy-1,5-pentylene, 2-phenyl-1,3-propylene or 2-(sulfophenyl)-1,3-propylene or a group of the formula

—(CH$_2$)$_2$—X—(CH$_2$)$_2$— or

—(CH$_3$)$_2$—X—(CH$_3$)$_2$— or

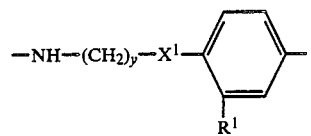

or

—(CH$_2$—CH$_2$—NH)$_n$—CH$_2$—CH$_2$— in which

X is an oxygen atom, a sulfur atom, the sulfonyl group or a group of the formula —NH—, —N(CH$_3$)— or —N(COCH$_3$)—, R$^1$ is hydrogen or sulfo, n is 2, 3 or 4, X$^1$ is the group —NH— or an oxygen atom, and y is 2 or 3, or W is 1,3-cyclohexylene, 1,4-cyclohexylene, bis-(cyclohex-1,4-ylene)-methane, 1,4-di-(methylene)-benzene, 1,3-di-(methylene)-benzene, 1,4-di-(1',2'-ethylene)piperidine, 1,4-phenylene, 1,3-phenylene, 4-methylene-1,4-phenylene or 4-ethylene-1,4-phenylene, and R* is hydrogen or alkyl of 1 to 4 carbon atoms, alkoxy of 1 to 5 carbon atoms, halogen, carboxy or sulfo.

2. A compound as claimed in claim 1 wherein R* is a hydrogen atom.

3. A compound according to claim 1, wherein R is hydrogen.

4. A compound according to claim 2, wherein R is hydrogen.

5. A compound according to claim 1, wherein W is para-phenylene or meta-phenylene.

6. A compound according to claim 2, wherein W is para-phenylen or meta-phenylene.

7. A compound according to claim 3, wherein W is para-phenylene or meta-phenylene.

8. A compound according to claim 1, wherein W is 1,2-ethylene, 1,3-propylene, 1,4-butylene or iso-propylene.

9. A compound according to claim 2, wherein W is 1,2-ethylene, 1,3-propylene, 1,4-butylene or iso-propylene.

10. A compound according to claim 3, wherein W is 1,2-ethylene, 1,3-propylene, 1,4-butylene or iso-propylene.

* * * * *